(12) United States Patent
Chui

(10) Patent No.: US 10,088,477 B2
(45) Date of Patent: Oct. 2, 2018

(54) BIOMOLECULAR DETECTION TEST STRIP DESIGN

(71) Applicant: The Regents of the University of California, Oakland, CA (US)

(72) Inventor: Chi On Chui, Encino, CA (US)

(73) Assignee: The Regents of the University of California, Oakland, CA (US)

( * ) Notice: Subject to any disclaimer, the term of this patent is extended or adjusted under 35 U.S.C. 154(b) by 430 days.

(21) Appl. No.: 14/418,408

(22) PCT Filed: Jul. 30, 2013

(86) PCT No.: PCT/US2013/052764
§ 371 (c)(1),
(2) Date: Jan. 29, 2015

(87) PCT Pub. No.: WO2014/022422
PCT Pub. Date: Feb. 6, 2014

(65) Prior Publication Data
US 2015/0204860 A1 Jul. 23, 2015

Related U.S. Application Data

(60) Provisional application No. 61/677,368, filed on Jul. 30, 2012.

(51) Int. Cl.
G01N 33/543 (2006.01)
G01N 27/414 (2006.01)
B01L 3/00 (2006.01)

(52) U.S. Cl.
CPC ........ *G01N 33/5438* (2013.01); *B01L 3/5027* (2013.01); *B01L 3/502715* (2013.01);
(Continued)

(58) Field of Classification Search
None
See application file for complete search history.

(56) References Cited

U.S. PATENT DOCUMENTS

2005/0212016 A1 9/2005 Brunner et al.
2007/0238186 A1* 10/2007 Sun ...................... C12Q 1/6874
436/94
(Continued)

FOREIGN PATENT DOCUMENTS

CN 101051037 A 10/2007
CN 101592626 A 12/2009
(Continued)

OTHER PUBLICATIONS

First Office Action for Chinese Application No. 2013800505156 dated Mar. 4, 2016.
(Continued)

*Primary Examiner* — Erik B Crawford
(74) *Attorney, Agent, or Firm* — Foley & Lardner LLP; Cliff Z. Liu

(57) ABSTRACT

Described here are a device and a method for detecting the presence of a biomarker using the device, wherein the device comprises (a) a substrate comprising a plurality of electrodes; (b) a plurality of nanowire field-effect transistor sensors integrated or assembled on the substrate and connected to the electrodes; and (c) a microfluidic component disposed on the substrate and adapted to communicate fluidically with the nwFET sensors.

3 Claims, 12 Drawing Sheets

(52) U.S. Cl.
CPC ..... *G01N 27/4145* (2013.01); *G01N 27/4146* (2013.01); *G01N 33/54353* (2013.01); *B01L 2200/10* (2013.01); *B01L 2300/0645* (2013.01); *B01L 2300/0681* (2013.01); *B01L 2300/0816* (2013.01); *B01L 2300/0864* (2013.01); *B01L 2300/16* (2013.01); *B01L 2400/0406* (2013.01); *B01L 2400/0683* (2013.01); *B01L 2400/0694* (2013.01); *G01N 27/4148* (2013.01)

(56) References Cited

U.S. PATENT DOCUMENTS

| | | |
|---|---|---|
| 2008/0063566 A1 | 3/2008 | Matsumoto et al. |
| 2008/0283875 A1 | 11/2008 | Mukasa et al. |
| 2009/0103091 A1 | 4/2009 | Jones et al. |
| 2010/0072976 A1 | 3/2010 | Sheu et al. |
| 2010/0140110 A1 | 6/2010 | Kim et al. |
| 2011/0165557 A1 | 7/2011 | Ah et al. |
| 2011/0215002 A1 | 9/2011 | Martinez |
| 2011/0237000 A1 | 9/2011 | Tey et al. |
| 2011/0275544 A1 | 11/2011 | Zhou et al. |
| 2011/0281288 A1* | 11/2011 | Chen .................. G01N 33/5438 435/15 |
| 2012/0040370 A1 | 2/2012 | Orwar et al. |

FOREIGN PATENT DOCUMENTS

| | | |
|---|---|---|
| CN | 102435655 A | 5/2012 |
| JP | 2002-239317 A | 8/2002 |
| JP | 2005-274574 A | 10/2005 |
| JP | 2007-255912 A | 10/2007 |
| WO | WO-02/059579 A1 | 8/2002 |
| WO | WO-2008/083687 A1 | 7/2008 |
| WO | WO-2011/102885 | 8/2011 |
| WO | WO-2012/075445 | 6/2012 |

OTHER PUBLICATIONS

Extended European Search Report and Search Opinion for European Application No. 13825713.4 dated Mar. 2, 2016.
Official Action for Japanese Patent Application No. 2015-525518 dated Jun. 5, 2017.
First Examination Report for Australian Patent Application No. 2013296563 dated May 24, 2017.
Third Office Action for Chinese Patent Application No. 2013800505156 dated Aug. 8, 2017.
Examination Report for European Application No. 13825713.4 dated Feb. 13, 2018.
Second Examination Report for Australian Application No. 2013296563 dated Mar. 5, 2018.
LV, Fangjun et al. (2010) "2. Method of Standard Curve", "Analytical Chemistry", Mid-China University of Science and Technology Press, 1st edition, Aug. 31, 2010, p. 144.
Rejection Decision for Chinese Patent Application No. 201380050515. 6, dated Apr. 10, 2018.
Examination Report for European Application No. 13825713.4, dated Jun. 29, 2018.

* cited by examiner (A) (B)

BIOMOLECULAR DETECTION TEST STRIP DESIGN

CROSS REFERENCE TO RELATED APPLICATION

This application is a National Stage Entry of PCT/US2013/052764 filed on Jul. 30, 2013, which claims the benefit of U.S. provisional application Ser. No. 61/677,368 filed Jul. 30, 2012, which is hereby incorporated by reference in its entirety.

BACKGROUND

Enzyme-linked immunosorbent assay (ELISA) is a lab-based in vitro diagnostic (IVD) tool and the clinical gold standard that detects the presence of target proteins, such as antigens or antibodies, in bio-specimens. This detection method can provide either a quantitative or qualitative result. This method is highly sensitive but requires significant capital equipment and a trained technician to operate as it typically requires multiple processing steps. ELISA is thus not portable and takes significant time to generate a result. These limitations collectively urge for new IVD technologies that permit cheaper, more frequent and more sensitive diagnostics to improve the clinical diagnostics cost-effectiveness and therapeutic outcomes.

SUMMARY

Many embodiments of the invention relate to a Semiconductor Electronic Label-Free Assay (SELFA) test strip device for biomolecular detection, comprising: (a) a substrate comprising a plurality of electrodes; (b) a plurality of electronic sensors, such as field-effect transistor (FET) sensors or nanowire field-effect transistor (nwFET) sensors, integrated or assembled on the substrate and connected to the electrodes; and (c) a microfluidic component disposed on the substrate and adapted to communicate fluidically with the electronic sensors.

In one embodiment, the microfluidic component comprises a sensing arm. In one embodiment, the microfluidic component further comprises a buffer reservoir upstream of the sensing arm. In one embodiment, the sensing arm comprises a sample reservoir, a sample filtration module downstream of the sample reservoir, and a sample sensing region downstream of the sample filtration module. The sample sensing region can be adapted to communicate fluidically with at least one of the electronic sensors.

In one embodiment, the microfluidic component further comprises a control arm. In one embodiment, the control arm is connected to the same buffer reservoir upstream of the sensing arm. In another embodiment, the control arm is connected to a separate buffer reservoir. In one embodiment, the control arm comprises an optional control reservoir, a control filtration module downstream of the optional control reservoir, and a control sensing region downstream of the control filtration module. The control sensing region can be adapted to communicate fluidically with at least one of the electronic sensors.

In one embodiment, the buffer reservoir comprises at least one buffer. The buffer can have an ionic strength of, for example, less than 200 mM, or less than 100 mM, or less than 50 mM, or less than 20 mM. The buffer can be released from the buffer reservoir into the sensing arm and/or the control arm to contact the electronic sensor.

Any filtration module adapted for filtering cells/debris from a biological sample can be used as the sample filtration module. In one embodiment, the sample filtration module is an inertial filtration module. The inertial filtration module can comprise, for example, a channel having a dimension larger than the cells/debris to be filtered. The inertial filtration module can comprise, for example, an expanding microchannel. The inertial filtration module can comprise, for example, (i) a focusing microchannel having a dimension smaller than the upstream channel to provide inertial lift forces, (ii) an expanding microchannel downstream of the focusing microchannel for guiding the cells/debris subjected to said inertial lift forces along the expanding channel wall, and (iii) a collection module downstream of the expanding microchannel for detouring the cells/debris into one or more side channels while allowing the rest of the biological sample to flow through and enter the sensing region.

Any filtration module adapted for filtering cells/debris from a biological sample can be used as the control filtration module. In one embodiment, the control filtration module is also an inertial filtration module.

In one embodiment, the microfluidic component further comprises at least one waste reservoir. The waste reservoir can be connected to the sensing arm and/or the control arm. One embodiment includes a first waste reservoir downstream of the sample sensing region and a second waste reservoir downstream of the control sensing region. Another embodiment includes a single waste reservoir downstream of both the sample sensing region and the control sensing region.

In one embodiment, the microfluidic component further comprises at least one reference reservoir. The reference reservoir can be connected to the sensing arm and/or the control arm. One embodiment includes a first reference reservoir upstream of the sample sensing region and a second reference reservoir upstream of the control sensing region. Another embodiment includes a single reference reservoir upstream of both the sample sensing region and the control sensing region. The reference reservoir can be, for example, placed downstream of the filtration module of the sensing arm and/or the control arm. The reference reservoir can comprise, for example, at least one reference solution of known concentration.

In one embodiment, the microfluidic component further comprises a capillary pump.

In one embodiment, the substrate of the test strip device comprises at least one polymer material. In another embodiment, the substrate comprises at least one semiconductor material.

In one embodiment, at least one of the electronic sensors is integrated on the substrate. In another embodiment, at least one of the electronic sensors is part of a chip assembled on the substrate. The test strip device can comprise at least 2, at least 4, at least 6, at least 12, or at least 48 electronic sensors integrated or assembled on the substrate.

In one embodiment, the test strip device further comprises a passivation layer atop the substrate and the electronic sensors disposed thereon and underneath the microfluidic channel. The passivation layer may expose only the sensing nanowire regions inside and electrical pads at the edges.

In one embodiment, at least one of the electronic sensors is an nwFET sensor that comprises a T-shaped structure comprising a latitudinal nanowire FET amplifier and a longitudinal sensing nanowire connected to the latitudinal nanowire FET amplifier. The latitudinal nanowire FET amplifier can have a first end connected to a source electrode and a second end connected to a drain electrode. The longitudinal sensing nanowire can have a first end connected to the latitudinal nanowire FET amplifier to form a node and a second end connected to a base electrode.

In one embodiment, the first end of the sensing nanowire is connected to the nanowire FET amplifier at an angle between about 10° and 170°, 40° and 140°, or 70° and 110° to form the node. The angle between the sensing wire and the nanowire FET amplifier can be about, less than about or greater than about 10°, 40°, 70°, 80°, 90°, 110°, 140°, or 170°. In another embodiment, the sensing nanowire is substantially orthogonal to the nanowire FET amplifier. In one embodiment, the sensing nanowire and the nanowire FET amplifier form an acute or obtuse angle. The angle referenced herein can be one of two angles formed between the sensing nanowire and nanowire FET amplifier. The two angles may be supplementary, such that the sum of the first and second angle is 180°. Alternatively, the two angles may not be supplementary. The two angles can be equal or unequal. For example, both angles can be about 45°, or one angle can be about 45° and the other can be about 90°.

In one embodiment, the sensing nanowire and the nanowire FET amplifier have about the same dimensions. In another embodiment, the width of the sensing nanowire and the nanowire FET amplifier are independently each within the range of about 10 nm to about 3000 nm, or within the range of about 50 nm to about 1000 nm, or within the range of about 100 nm to about 500 nm.

In one embodiment, the nwFET sensor further comprises a second sensing nanowire having a first end and a second end, wherein the first end of the second sensing nanowire is connected to the nanowire FET amplifier to form a node, and the second end of the second sensing nanowire is connected to a second base electrode. In one embodiment, the first sensing nanowire and the second sensing nanowire are connected to the nanowire FET amplifier at the same node.

In one embodiment, the nwFET sensor further comprises a third sensing nanowire having a first end and a second end, wherein the first end of the third sensing nanowire is connected to the nanowire FET amplifier to form a node, and the second end of the third sensing nanowire is connected to a third base electrode.

In one embodiment, the nwFET sensor can be shielded from the ambience via passivation, except for the sensing nanowire surfaces and optionally the surfaces of and near the node connecting the sensing nanowire and the nanowire FET amplifier.

In one embodiment, the sensing nanowire surface, and optionally the surface of and near the node connecting the said sensing nanowire and the nanowire FET amplifier, is derivatized with a plurality of immobilized receptors. The immobilized receptors can comprise free amino groups, free carboxyl groups, free hydroxyl groups, or a combination thereof.

In one embodiment, the sensing nanowire surface, and optionally the surface of and near the node connecting the said sensing nanowire and the nanowire FET amplifier, comprises a receptor immobilized thereon adapted to bind to a biomarker. Any biomarkers useful for clinical diagnostic applications can be targeted.

In one embodiment, the receptor can bind to a biomarker associated with immunomodulation and suppression in bone marrow transplant, such as CD4, CD14, CD25, forkhead box protein P3 (FoxP3), granzyme B, inhibitor of nuclear factor kappa-B kinase subunit beta (IKKβ), interferon-alpha (IFN-α), IFN-γ, interleukin 2 (IL-2), IL-4, IL-6, IL-10, IL-12, IL-17, monocyte chemoattractant protein-1 (MCP-1), myeloid differentiation primary response gene 88 (MyD88), nuclear factor kappa B (NFκB), perforin, TIR-domain-containing adapter-inducing interferon-β (TRIF), toll-like receptor 4 (TLR4), transforming growth factor-beta (TGF-β), and tumor necrosis factor-alpha (TNF-α).

In another embodiment, the receptor can bind to a biomarker associated with innate immunity in allorejection of bone marrow cells, such as FoxP3, heat shock protein (HSP), high-mobility group 1 box 1 protein (HMGB1), hyaluronan, Type I IFN, IFN-α, IFN-β, IFN-γ, interferon gamma-induced protein 10 (IP-10), interferoninduced protein with tetratricopeptide repeats 1 (Ifit1), Ifit2, IL-1β, IL-2, IL-4, IL-6, IL-10, IL-12, IL-17, IL-21, IL-23, MCP-1, MyD88, Regulated upon activation, normal T-cell expressed, and secreted (RANTES), TLR4, TRIF, and TNF-α.

In a further embodiment, the receptor can bind to a biomarker associated with skeletal muscle injuries and regeneration, such as creatine kinase, fatty acid binding protein (FABP), muscle troponin, myoglobin, and myosin light chain 1 (MLC-1). In a further embodiment, the receptor can bind to a biomarker associated with vascular injuries and regeneration, such as C-reactive protein (CRP), E-Selectin, intercellular adhesion molecule 1 (ICAM-1), ICAM-3, PSelectin, serum amyloid protein A (SAA), thrombomodulin, and vascular cell adhesion molecule 1 (VCAM-1). In an additional embodiment, the receptor can bind to a biomarker associated with spinal cord injuries and regeneration, such as CRP, erythropoietin (EPO), IL-2, IL-2 receptor (IL-2R), IL-8, leptin, matrix metalloproteinase 9 (MMP-9), MCP-1, neuron-specific enolase (NSE), phosphorylated neurofilament-H (pNFH), S100 calcium binding protein B (S100B), and TNF-α. In an additional embodiment, the receptor can bind to a biomarker associated with spinal nerve root injuries and regeneration, such as cystatin C, vitamin D-binding protein (DBP), hyaluronan, MMP-9, neurofilament light subunit (NFL), nociceptin, S100, soluble TNF receptor 1 (sTNFR1), tetranectin, and TNF-α.

In one embodiment, the plurality of nwFET sensors of the device can bind to at least 2, at least 4, at least 6, or at least 12 different biomarkers to simultaneously detect their presence in a sample.

In one embodiment, the device comprises: (a) a substrate comprising a plurality of electrodes; (b) a plurality of nanowire field-effect transistor (nwFET) sensors embedded or disposed on the substrate and connected to the electrodes, wherein each of the nwFET sensors comprises a T-shaped structure comprising a latitudinal nanowire FET amplifier and a longitudinal sensing nanowire connected to the latitudinal nanowire FET amplifier, wherein the sensing nanowire, and optionally also the node connecting the said sensing nanowire and nanowire FET amplifier, comprises receptors immobilized thereon, and wherein the nanowire FET amplifier is passivated; and (c) a microfluidic component disposed on the substrate and adapted to communicate fluidically with the nwFET sensors, the microfluidic component comprising: (i) at least one buffer reservoir comprising at least one buffer; (ii) at least one sensing arm connected to the at least one buffer reservoir, the sensing arm comprising a sample reservoir, a sample filtration module comprising at least one channel having a dimension larger than a cell to be filtered, and a sample sensing region adapted to communicate fluidically with at least one of the nwFET sensors; (iii) at least one control arm connected to the at least one buffer reservoir, the control arm comprising a control filtration module, a control sensing region adapted to communicate fluidically with at least one of the nwFET sensors, and optionally a control reservoir; and (iv) at least one waste reservoir connected to the sensing arm and the control arm, and wherein the microfluidic component defines a flow direction from (i) to (iv).

In one embodiment, the test strip device outputs are downloadable via an interface device to an electronic device.

Further embodiments of the invention relate to a method for detecting the presence of a biomarker, comprising: (A) providing a device comprising (a) a substrate comprising a plurality of electrodes, (b) a plurality of electronic sensors, such as field-effect transistor (FET) sensors or nanowire field-effect transistor (nwFET) sensors, integrated or assembled on the substrate and connected to the electrodes, and (c) a microfluidic component disposed on the substrate and adapted to communicate fluidically with the electronic sensors; and (B) introducing a biological sample to the microfluidic component, wherein the microfluidic component directs the flow of the biological sample to contact at least one of the electronic sensors, and wherein the presence of the biomarker results in a signal change at the at least one of the electronic sensors.

In one embodiment, the microfluidic component comprises at least one sensing arm connected to at least one buffer reservoir comprising at least one buffer; wherein the sensing arm comprises a sample reservoir for receiving the biological sample, a sample filtration module, and a sample sensing region adapted to communicate fluidically with at least one of the electronic sensors; and wherein the biological sample is introduced into the sample reservoir to contact a stream of the buffer flowing from the buffer reservoir.

In one embodiment, the method further comprises releasing the buffer from the buffer reservoir before introducing the biological sample.

In one embodiment, the sample filtration module is adapted for inertial filtration, and wherein the biological sample mixed with the buffer is filtered by the filtration module before entering the sample sensing region.

In one embodiment, the microfluidic component further comprises at least one control arm connected to the at least one buffer reservoir; wherein the control arm comprises a control filtration module, a control sensing region adapted to communicate fluidically with at least one of the nwFET sensors, and optionally a control reservoir; and wherein the biological sample is not introduced into the control reservoir.

In one embodiment, at least one of the electronic sensors is an nwFET sensor that comprises a T-shaped structure comprising a latitudinal nanowire FET amplifier and a longitudinal sensing nanowire connected to the latitudinal nanowire FET amplifier, and wherein the sensing nanowire comprises at least one receptor immobilized thereon adapted to bind to the biomarker.

In one embodiment, the method further comprises contacting at least one of the electronic sensors with a first reference solution comprising a lower concentration of the biomarker than the biological sample, which results in a first signal change in at least one of the electronic sensors serving as a first reference point for the quantification of the biomarker in the biological sample. In one embodiment, at least two, at least three, or at least four different reference solutions comprising lower concentrations of the biomarkers are used to generate reference points for the quantification of the biomarker in the biological sample.

In one embodiment, the method further comprises contacting at least one of the electronic sensors with a second reference solution comprising a higher concentration of the biomarker than the biological sample, which results in a second signal change in at least one of the electronic sensors serving as a second reference point for the quantification of the biomarker in the biological sample. In one embodiment, at least two, at least three, or at least four different reference solutions comprising higher concentrations of the biomarkers are used to generate reference points for the quantification of the biomarker in the biological sample.

In one embodiment, the first and/or second reference solutions are introduced to the microfluidic component which directs the flow of the first and second reference solutions to contact the electronic sensors. In one embodiment, the first and/or second reference solutions are preloaded into one or more reference reservoirs upstream of the sample sensing region of the sensing arm and/or upstream of the control sensing region of the control arm, wherein they are adapted to enter the sensing region before and/or after the introduction of the biological sample.

In one embodiment, the method comprises (A) providing a device, comprising (a) a substrate comprising a plurality of electrodes; (b) a plurality of nanowire field-effect transistor (nwFET) sensors embedded or disposed on the substrate and connected to the electrodes, wherein each of the nwFET sensors comprises a T-shaped structure comprising a longitudinal sensing nanowire connected to a latitudinal nanowire FET amplifier, wherein the sensing nanowire, and optionally also the node connecting the said sensing nanowire and nanowire FET amplifier, comprises a receptor immobilized thereon adapted to bind to the biomarker, and wherein the nanowire FET amplifier is passivated; and (c) a microfluidic component disposed on the substrate and adapted to communicate fluidically with the nwFET sensors, the microfluidic component comprising: (i) at least one buffer reservoir comprising at least one buffer; (ii) at least one sensing arm connected to the at least one buffer reservoir, the sensing arm comprising a sample reservoir, an sample filtration module comprising at least one channel having a dimension larger than a cell to be filtered, and a sample sensing region adapted to communicate fluidically with at least one of the nwFET sensors; (iii) at least one control arm connected to the at least one buffer reservoir, the control arm comprising an optional control reservoir, a control filtration module, and a control sensing region adapted to communicate fluidically with at least one of the nwFET sensors; and (iv) one or more waste reservoirs connected to the sensing arm and the control arm, and wherein the microfluidic component defines a flow direction from (i) to (iv); (B) releasing the buffer from the buffer reservoir; and (C) adding a biological sample to the sample reservoir to contact a stream of the buffer flowing from the buffer reservoir; wherein the biological sample mixed with the buffer is filtered by the sample filtration module before entering the sensing region; and wherein the biological sample mixed with the buffer contacts the sensing nanowire of the nwFET sensor at the sample sensing region, and wherein a binding between the biomarker and the receptor immobilized on the sensing nanowire results in a signal change at the at least one of the nwFET sensors.

Additional embodiments of the invention relate to a method for immobilizing a receptor, comprising (A) disposing a microfluidic layer on a substrate comprising a plurality of electrodes and a plurality of electronic sensors, such as field-effect transistor (FET) sensors or nanowire field-effect transistor (nwFET) sensors, connected to the electrodes, wherein the microfluidic layer comprises a plurality of channels adapted to communicate fluidically with the electronic sensors; and (B) adding a solution of the receptor into at least one of the channels, wherein the receptor contacts and binds to at least one of the electronic sensors. In one embodiment, at least 2, at least 4, at least 6, or at least 12 different receptors are concurrently and selectively immobilized on the plurality of electronic sensors.

At least one advantage of at least some embodiments described herein is that no bulky optical infrastructure is required due to an imaging-free sensing modality. Compared to selected optical assays, the need for fluorescence labeling, and thus additional reagents and conjugation steps can be excluded.

At least another advantage of at least some embodiments described herein is that little or no electrochemical enzyme-based amplification is involved such that enzyme reagents and their conjugations are no longer necessary. A very rapid turn-around time (TAT) is therefore anticipated for bedside administration.

At least another advantage of at least some embodiments described herein is that the test strip platform can directly interface with readout electronics such that no skilled personnel are needed, in contrast to clinical ELISA tests.

At least a further advantage of at least some embodiments described herein is the easy-to-handle microfluidics, which can be preloaded with buffer solution and filters out cells/debris based on inertial filtration. It is robust and clog-resistant because inertial filtration operates with channel dimensions larger than the cells-debris to be removed.

At least a further advantage of at least some embodiments described herein is the robust detection procedures, which comprises target analyte binding in physiological fluid as the first step and biomolecular-to-electrical signal transduction in purified low-ionic strength buffer as the second step. This mitigates the charge screening issue prohibitive to other FET-based sensing solutions, and simultaneously alleviates the non-specific competitive binding problem with interfering analytes.

At least an additional advantage of at least some embodiments described herein is the self-referenced data acquisition platform. The test strip dual-arm design permits differential measurements to be taken between the sensing arm with target analytes and interferents, and the control arm with substantially only purified buffer. This design can effectively suppress any systematic and/or ambient fluctuations induced measurement errors, and can enhance the overall detection signal-to-noise (SNR) ratio.

DETAILED DESCRIPTION

All references cited herein are hereby incorporated by reference in their entireties.

While certain conditions and criteria are specified herein, it should be understood that these conditions and criteria apply to some embodiments of the disclosure, and that these conditions and criteria can be relaxed or otherwise modified for other embodiments of the disclosure.

While the invention has been described with reference to the specific embodiments thereof, it should be understood by those skilled in the art that various changes may be made and equivalents may be substituted without departing from the true spirit and scope of the invention as defined by the appended claim(s). In addition, many modifications may be made to adapt a particular situation, material, composition of matter, method, operation or operations, to the objective, spirit and scope of the invention. All such modifications are intended to be within the scope of the claim(s) appended hereto. In particular, while certain methods may have been described with reference to particular operations performed in a particular order, it will be understood that these operations may be combined, sub-divided, or re-ordered to form an equivalent method without departing from the teachings of the invention. Accordingly, unless specifically indicated herein, the order and grouping of the operations is not a limitation of the invention.

Test Strip Device

Figure 1:
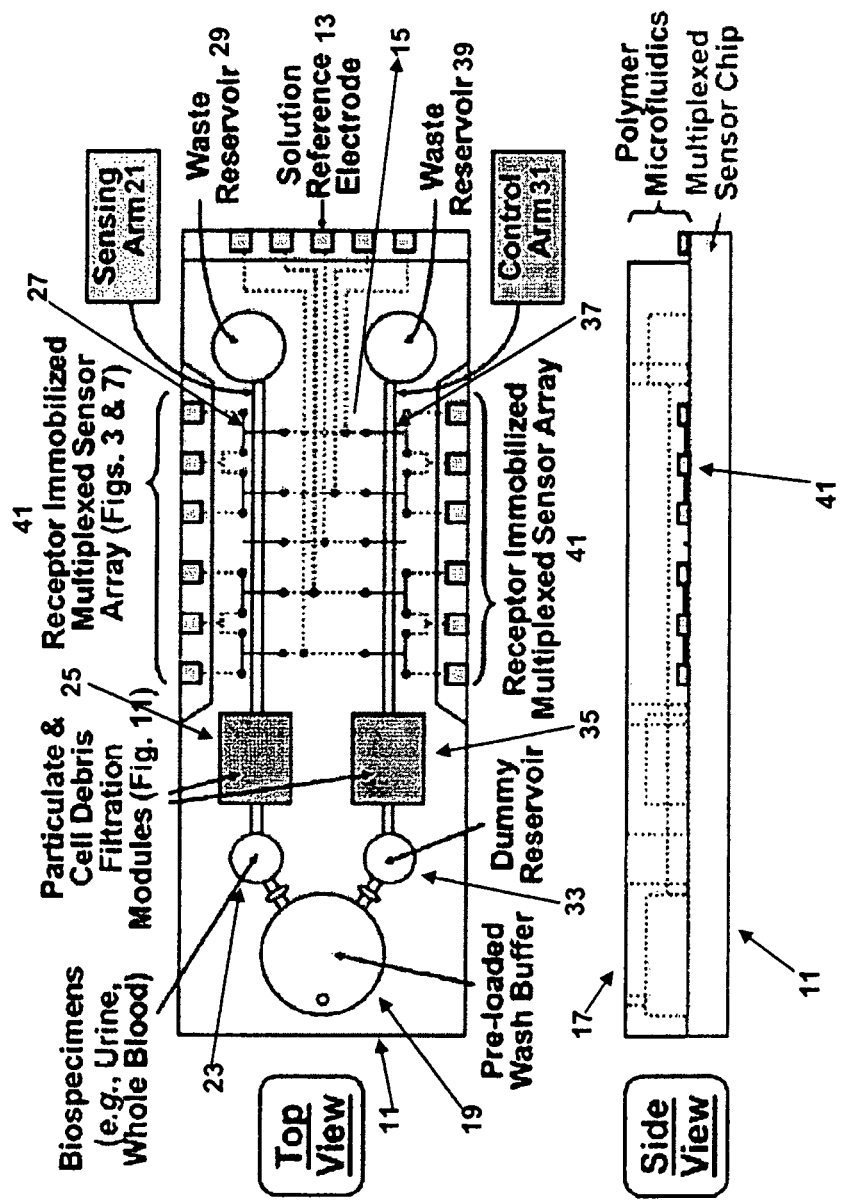
FIG. 1 shows an example of a Semiconductor Electronic Label-Free Assay (SELFA) test strip architecture including both top view and side view. It comprises polymer handling micro-fluidics assembled above a multiplexed sensor semiconductor (or polymer) chip. Electrodes are accessible from the top for SELFA interface contact.

As shown in FIG. 1, the SELFA test strip device described herein can comprise a microfluidic component (17)

assembled atop a test strip substrate (11) embedded thereon multiplexed electronic sensors such as nwFET biosensors (41) pre-immobilized with respective specific receptors. The test strip substrate can be, for example, a rigid silicon wafer with integrated electronic sensors or a bendable polymer for small sensor chips assembly. The easy-handling microfluidic component can allow seamless sample preparation and movement through the system with minimal user action and no bulky mechanized pumps.

The substrate (11) can comprise, for example, a plurality of electrodes (13). The electronic sensors (41) and the electrodes (13) can be connected via electrical interconnections (15).

The microfluidic component (17) can comprise, for example, a buffer reservoir (19) for holding a buffer, and a sensing arm (21) and a control arm (31) downstream of the buffer reservoir (19). The sensing arm (21) can comprise, for example, a sample reservoir (23) for receiving a biological sample, a sample filtration module (25), and a sample sensing region (27) adapted to communicate fluidically with at least one of the electronic sensors. The control arm (31) can comprise, for example, an optional control reservoir (33) or dummy reservoir, a control filtration module (35), and a control sensing region (37) adapted to communicate fluidically with at least one of the electronic sensors. The microfluidic component can further comprise, for example, one or more waste reservoirs (29, 39) downstream of the sensing arm (21) and the control arm (31).

The SELFA test strip device can be pre-loaded with most necessary reagents such that no or minimal additional reagent is required to be introduced by the end-user, other than the biological sample or bio-specimen. The unique combination of novel nanoelectronic biosensors, data acquisition in low-salt control buffer, and differential measurements against a built-in control can yield high detection sensitivity. The "sensing-in-buffer" procedure can also give rise to high detection specificity due to the substantial absence of cross-reacting interferents as well as the fast desorption kinetics of the pre-bound interferents. After sampling, the SELFA test strip device can be inserted into a common interface (e.g., USB) for readout via the user's computer or smart phone. The SELFA test strip device can be disposable for hygienic reasons yet the device itself contains no bio-hazardous materials and can be recycled through proper recollection. The SELFA test strip device can be operated by a one-step or multi-step testing procedure which does not require trained personnel to perform or bio-specimen transportation back to a centralized laboratory. Moreover, the SELFA test strip device permits concurrent quantification of multiple biomarker concentrations with a TAT of less than 20 min from <100 μL of the user's serum or bodily fluid.

Figure 2:
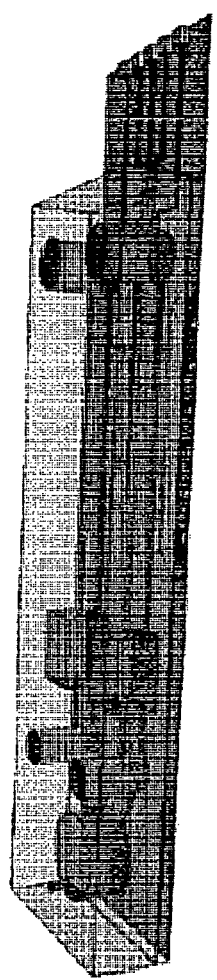
FIG. 2 shows (A) design sketch and (B) chip photo of an example of a SELFA test strip, which is capable of performing multiplexed in vitro diagnostics for clinical diagnostic applications such as post-transplantation immunity assessment and injury biomarker panels.
Figure 2:
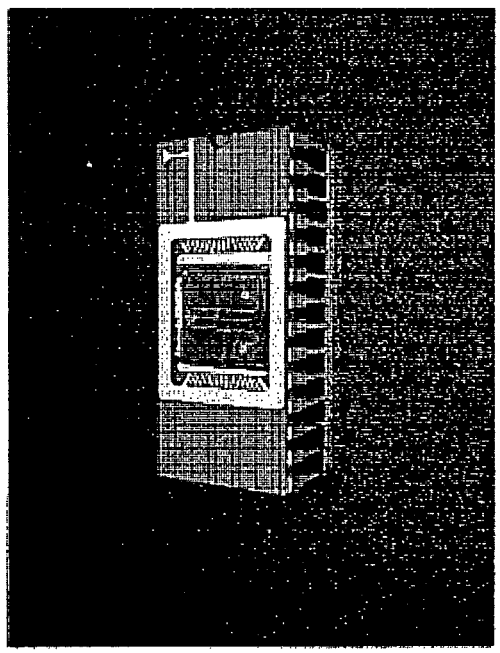
Figure 3:
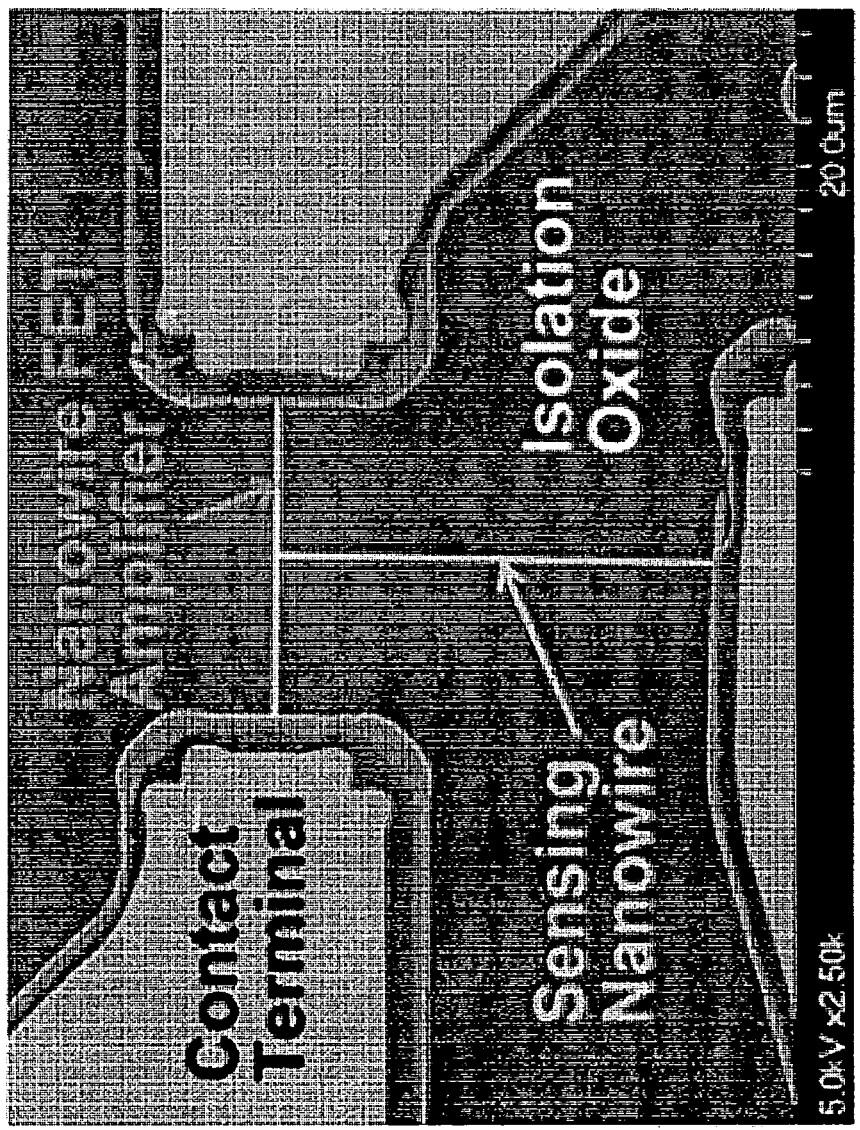
FIG. 3 shows a scanning electron micrograph (SEM) of an example of a T-nwFET sensor with high sensitivity.

The innovative and unique features of the SELFA test strip device described herein includes the following: (I) Novel nanoelectronic biosensors: The innovative nwFET sensor structure seamlessly integrates therein a sensing nanowire and a nanowire FET amplifier (FIG. 3). Occurring at the sensor front-end, biomolecular detections and low-noise amplification of the transduced electrical signals can substantially enhance the sensor-level sensitivity, which in turn can lower both limit of detection (LOD) and limit of quantitation (LOQ). Besides, the sensitivity and dynamic range (DR) attributes are electrically tunable at runtime if necessary. (II) Simple handling microfluidics: The innovative fluidic architecture combines sequentially programmed capillary flows with inertial filtration of cells/debris. This unique combination can provide a simple actuation after loading of the sample to analyze, can require little or no additional power, and can be robust and clog-resistant because inertial filtration operates with channel dimensions larger than the cells/debris to be removed. (III) Robust detection procedure: The procedure comprises target analyte binding in physiological fluid as the first step and biomolecular-to-electrical signal transduction in purified low-ionic strength buffer as the second step. This can mitigate the charge screening issue prohibitive to other FET-based sensing solutions, while simultaneously alleviating the non-specific competitive binding problem with interfering analytes. (iv) Self-referenced data acquisition platform: The SELFA test strip dual-arm design permits differential measurements to be taken between the sensing arm with target analytes and interferents, and the control arm with substantially only purified buffer (FIG. 2). This design can effectively suppress systematic and/or ambient fluctuations induced measurements errors, and thus can enhance the overall detection signal-to-noise (SNR) ratio. An optional step can be added at the end to introduce one or more reference solutions of known concentrations, from one or more pre-loaded reference reservoirs upstream of the sample sensing region and/or the control sensing region, to improve quantification performance.

Nanowire Field-Effect Transistor Sensor

Either integrated or assembled on a substrate, the nwFET sensor described herein can comprise a T-shaped structure comprising a latitudinal nanowire FET amplifier and a longitudinal sensing nanowire connected to said latitudinal nanowire FET amplifier (denoted as T-nwFET). In some embodiments, the T-nwFET can be implemented as described in detail in WO 2012/075445, which is hereby incorporated by reference in its entirety.

The nwFET sensor, in one embodiment, comprise at least one sensing nanowire having a first end and a second end. The first end of the sensing nanowire connects with the nanowire FET to form a node, and the second end of the sensing nanowire is connected to a base electrode. The at least one sensing nanowire and nanowire FET each comprise at least one semiconductor material. The at least one sensing nanowire, in one embodiment, is a straight nanowire, curved nanowire, serpentine nanowire, or in the shape of an "L". Various architectures of the nwFET sensors can be used. In one embodiment, the device of the invention comprises at least two sensing nanowires, and the two sensing nanowires are connected to the nwFET at the same node. In another embodiment, the device of the invention comprises at least two sensing nanowires, and the two sensing nanowires are connected to the nwFET at different nodes.

In some embodiments, a Y-shape nwFET sensor can be used instead of or in addition to a T-shape nwFET sensor. Rather than being a straight nanowire, the nanowire FET described herein can also be a curved nanowire, a serpentine nanowire, in the shape of an "L", in the shape of an "V", or else. The sensing nanowire can be connected to any place along the nanowire FET, and at any possible angle which could be beyond the range of 0 to 180. If the nanowire FET has the shape of an "L" or "V", the sensing nanowire can be connected to the corner of the "L" or "V", or anywhere else along the nanowire FET to form the node, and at any possible angle which could be beyond the range of 0 to 180.

This innovative sensor structure embraces the large surface area-to-volume ratio advantage while offering close-proximity signal amplification with low parasitics as explained below. The entire sensor can be shielded from the ambience via passivation, except for the sensing nanowire surface. The specific receptors can be immobilized only onto the sensing nanowire surface. The biomarker present in the sample solution can be bound to the receptors with high specificity. The electric field emanated from the bound analyte charges can then be coupled to modulate the sensing nanowire conductance. The resultant signal change can be amplified with minimal parasitics by the built-in, orthogonal nanowire FET amplifier to attain high sensitivity, and then electronically read out.

Figure 4:
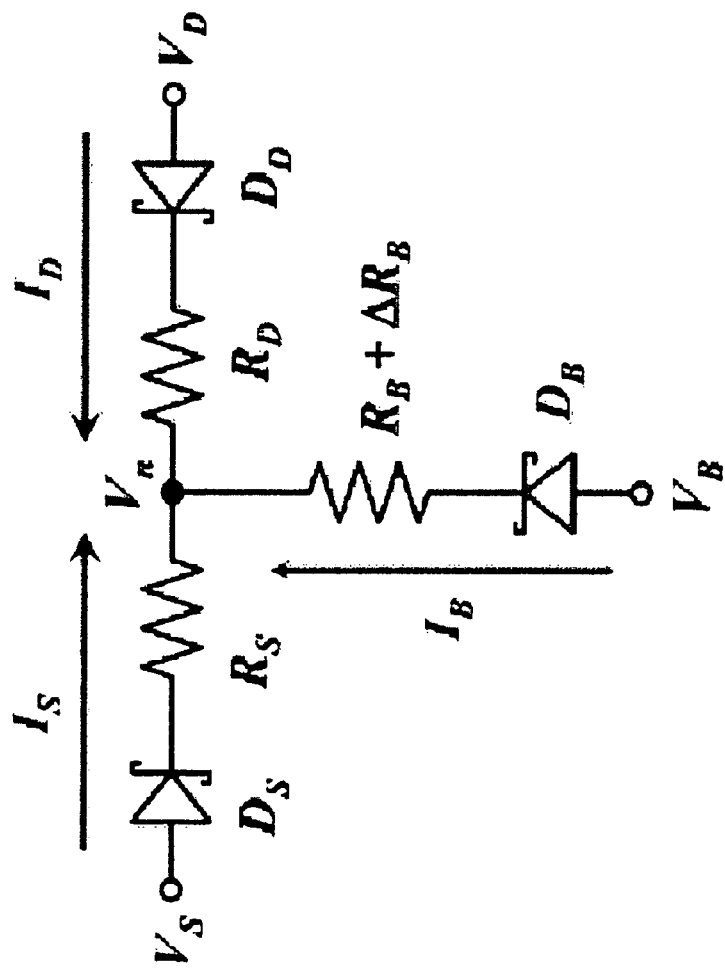
FIG. 4 shows an equivalent circuit of an example of a T-nwFET sensor.

The intrinsic signal transduction and amplification mechanism in this T-nwFET sensor can be understood with the help of the equivalent circuit illustrated in FIG. 4. The node potential at the intersection is labeled as $V_n$ and each nanowire segment from this node to the respective electrode is represented as a nanowire resistance (Rx) in series with an ideal Schottky diode ($D_x$). The sensing nanowire and FET drain current are respectively related to the electrode potentials (e.g., $V_B$ and $V_D$) by $$I_B = I_0 \left[ \exp\left( \frac{q((V_B - V_n) - I_B(R_B + \Delta R_B))}{k_B T} \right) - 1 \right] \quad (1)$$

$$I_D = I_0 \left[ \exp\left( \frac{q((V_D - V_n) - I_D R_D)}{k_B T} \right) - 1 \right] \quad (2)$$

$$I_0 = AA^{**} T^2 \exp\left( -\frac{q\phi_{Bp}}{k_B T} \right) \quad (3)$$

Since identical Schottky contacts are represented in FIG. 4, the amplification ratio ($dI_D/dI_B$) can be largely determined by the nanowire resistances $R_B$ and $R_D$, and externally applied potentials $V_D$ and $V_B$. During the sensing operation, both the drain ($V_D$) and base ($V_B$) contacts can be biased positively against the source contact. The modulation of sensing nanowire conductance due to specific binding of target analytes can yield a non-zero $\Delta R_B$ value, and thus can change the $I_B$ according to Equation 1. That in turn can vary the potential $V_n$ and modify the semiconductor energy band profile between the source and drain contacts. The resultant change in the voltage difference ($V_D - V_n$) can yield an exponential change in $I_D$ such that an amplification of the detected signal can be achieved.

Substrate and Sensor Configuration

Figure 7:
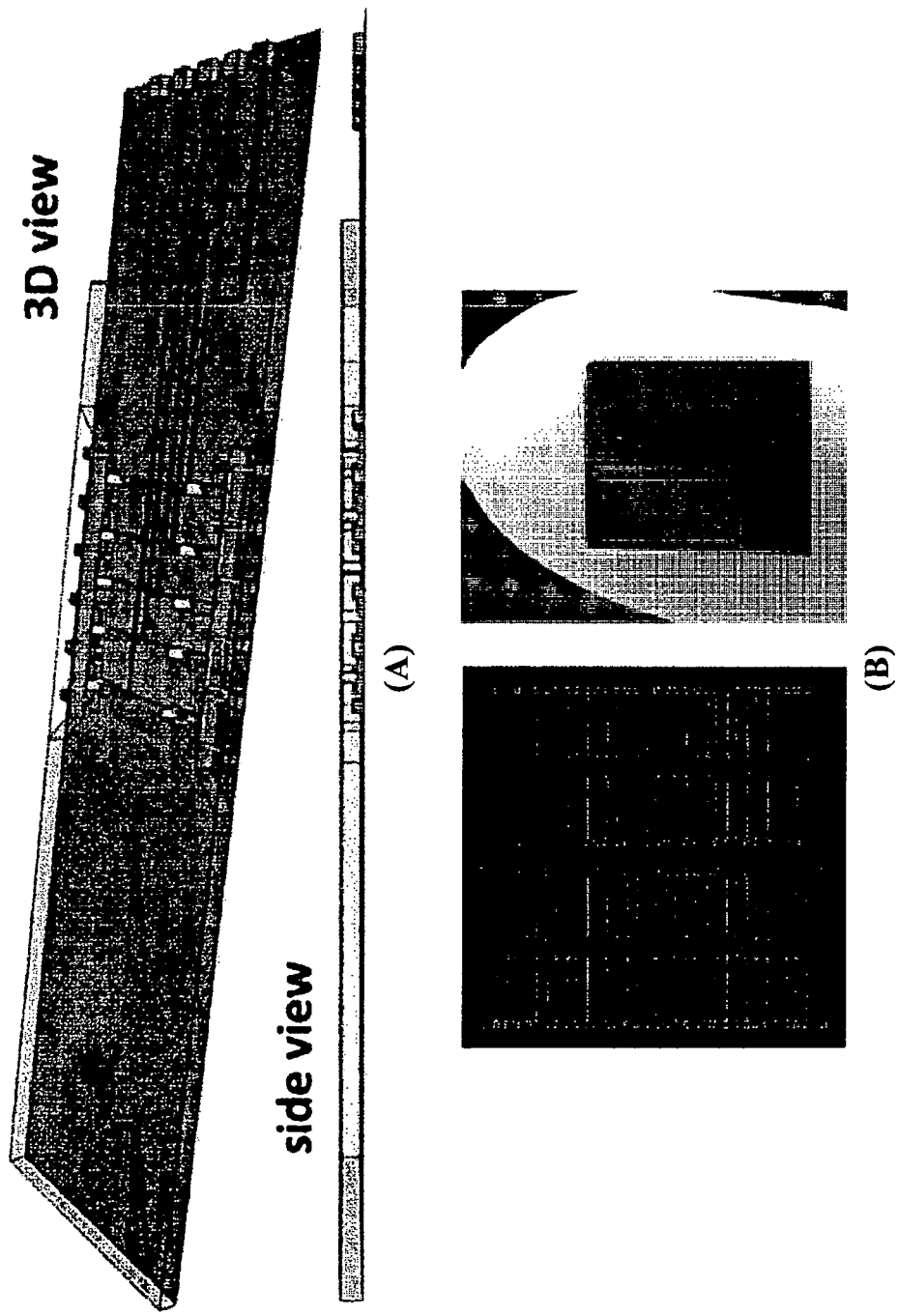
FIG. 7 shows an example of a test strip substrate configuration. (A) The images are an example of outlook sketches showing integrated multiplexed nwFET biosensor array and electrical interconnection onto the same rigid silicon wafer platform (in brown). The transparent layer atop is a passivation layer exposing only the sensing nanowire regions (see FIG. 3) inside and contact pads in the periphery. (B) The images are the nanofabrication layout and chip photo of a fabricated example device of the multiplexed biosensor array portion of the test strip.
Figure 8:
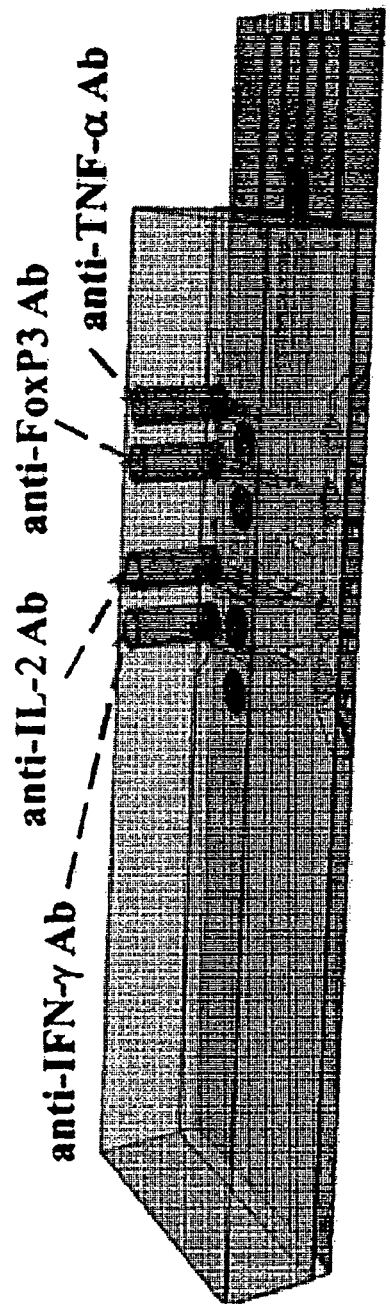
FIG. 8 shows an example of concurrent and selective receptor immobilization scheme. Attached above the test strip surface, a microfluidic layer with parallel and separated inlets, channels, and outlets facilitates concurrent and selective immobilization of specific receptors (e.g., antibodies to IFN-γ, IL-2, FoxP3, TNF-α) to each individual nwFET biosensor within the multiplexed array.

There are at least two configurations that the nwFET sensors can be disposed on the test strip substrate. In the first configuration, an array of multiplexed nwFET biosensors, together with electrical interconnections, can be simultaneously fabricated onto a rigid wafer platform, such as a silicon-based wafer, as shown in FIG. 7A. FIG. 7B shows a nanofabrication layout of the multiplexed nwFET biosensor array portion of the test strip as well as the chip photo of a fabricated prototype. The test strip chip surface can be capped with a passivation layer (FIG. 7A) to prevent electrical shorts by exposing only the sensing nanowire regions inside and electrical pads at the edges. For concurrent and selective immobilization of specific receptors onto each individual nwFET biosensor within the multiplexed array, a microfluidic structure with parallel inlets, channels, and outlets can be adhered on the test strip surface, as shown in FIG. 8, followed by reagents introduction. This microfluidic layer can be peeled off from the surface after the receptor immobilization step.

Figure 9:
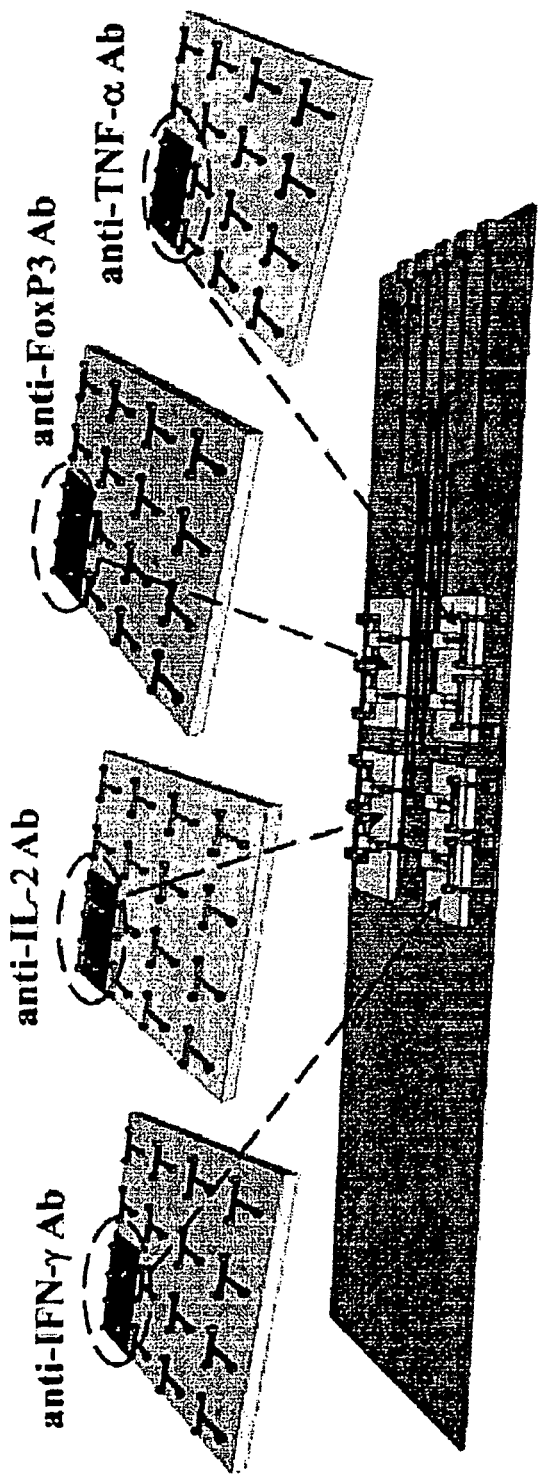
FIG. 9 shows an example of an assembly of pre-fabricated nwFET biosensor chips, with different and separate receptor immobilizations (e.g., antibodies to IFN-γ, IL-2, FoxP3, TNF-α), into a single polymer substrate platform. Electrical interconnections are formed post-assembly.
Figure 10:
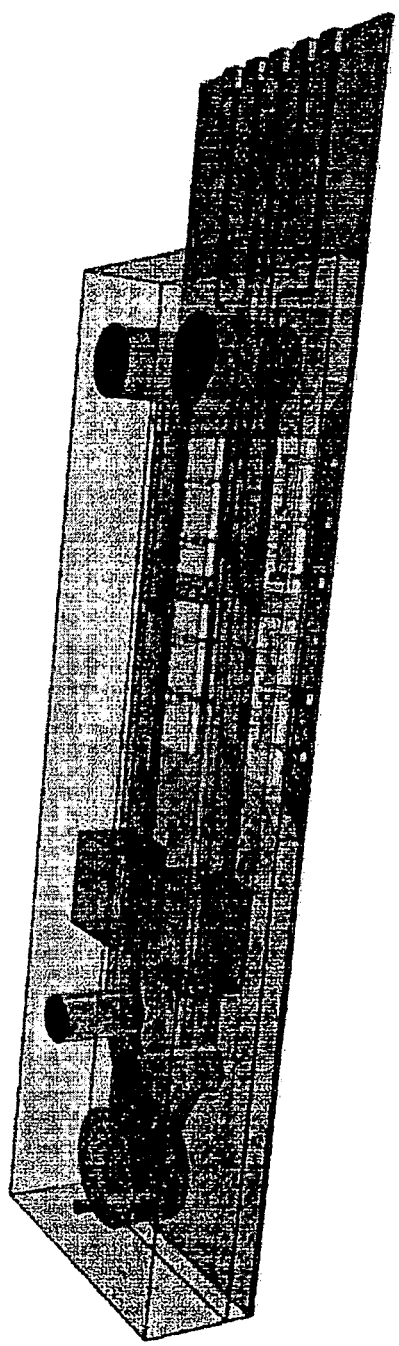
FIG. 10 shows an example outlook sketch of a SELFA test strip. This configuration has the polymer substrate embedded thereon an array of receptor pre-immobilized nwFET biosensor chips. The simple handling microfluidics is attached on the top surface.

In the second configuration, an array of pre-fabricated and receptor pre-immobilized nwFET biosensor chips can be assembled onto a test strip substrate, which can be a polymer substrate. For example, FIG. 9 shows an assembly of several nwFET biosensor chips pre-immobilized with different receptors. The electrical interconnections between the assembled nwFET biosensors and edge pads can be subsequently formed, followed by the synthesis of a surface passivation layer. Compared to the first configuration, the substrate in the second configuration, assembled with receptor-immobilized nwFET biosensors, can be smaller in size. The second configuration also does not require microfluidic-assisted receptor immobilization as depicted in FIG. 8. On the other hand, compared to the first configuration, the second configuration may involve more manufacturing engineering for the on-strip electrical interconnections to the assembled nwFET biosensor chips.

Receptor Immobilization

The SELFA test strip device described herein is versatile and can allow concurrent multiplexed detection of a wide variety of biomarkers, whether antigens or antibodies, upon identification and optimal immobilization of specific receptor molecules on the sensing nanowire surface (FIG. 3). Antibody or antigen receptors employed in commercial ELISA kits can be adopted. For their immobilizations onto the nwFET biosensor surface, the hydroxyl termination on the silicon nanowire surface can be first converted to amine termination via, for instance, 3-aminopropyltriethoxysilane (APTES) functionalization. The amine termination can be further converted to aldehyde termination with, for instance, glutaraldehyde functionalization for the subsequent antibody immobilization. The aforementioned cross-linker combination was adopted to generate the label-free PSA, cTnI, and IL-1β detection data shown in Working Example 1. However, other cross-linkers known in the art can also be used, such as N-maleimidobutyryloxy succinimide ester (GMBS) coupling agent.

Microfluidic Component

The microfluidic component of the SELFA test strip device described herein innovatively combines sequentially-driven capillary flows with inertial filtration of cells and debris. This unique combination can provide an actuation after loading of the sample to analyze, can require no additional power, and can be robust and clog-resistant because inertial filtration can operate with channel dimensions larger than the cells/debris to be removed.

The operation of the system can be classified into three parts: (i) actuation to initiate wash buffer flow, (ii) sample loading, and (iii) sample flow. A cartridge or reservoir will have a pre-loaded wash buffer with low ionic strength in a membrane bound capsule. In some embodiments, the first step in running the assay is to puncture this capsule and remove the puncture button. Alternatively, the buffer can be released by removing a valve downstream of the buffer reservoir.

This actuation action can initiate capillary flow through one or more microfluidic channels, which can be hydrophilic, by (a) allowing a vent to atmospheric pressure and (b) providing a flow path through the channel. After the wash buffer reaches the sample reservoir, a biological sample (e.g., a drop of bodily fluid or blood) can be introduced. The biological sample diluted with the wash buffer can be drawn through narrow microchannels of a filtration module where inertial and deformability-induced lift forces push cells and larger particles away from the channel wall and centerline. Streams of diluted biological sample without particulate are then available to flow over the sensing region to contact the nwFET sensors. Continuing flow of wash buffer driven by downstream large-volume capillary pumps can wash the sensing regions to be occupied by low conductivity buffer for measurements. The volume of the capillary can be optimized to allow sampling of about 100 μL or less or more of sample followed by about 2 mL or less or more of wash buffer. The sensing arm and the control arm can be washed in parallel to obtain a differential measurement (see FIG. 1).

Buffer

Since the high ionic strength in physiological fluid can be prohibitive to practical FET-based sensing due to charge screening, changing the sensing solution to a low-salt buffer can be an effective solution. Moreover, differential measurements across two parallel analytical arms (FIG. 1, sensing arm and control arm), one for target analytes capture and the other for wash buffer flow only, can give rise to high fidelity signal transduction with suppressed errors caused by systematic and/or ambient fluctuations. The buffer salt concentration can be, for example, less than 200 mM, or less than 100 mM, or less than 50 mM, or less than 20 mM.

At the same time, high detection selectivity can be achieved with the same "sensing-in-buffer" procedure. When the sensing solution is changed from filtered serum (or other bodily fluid) to purified buffer, many non-specific interferents are substantially absent, whereby avoiding competitive non-specific binding. The use of flowing, instead of stationary, buffer together with a polyethylene glycol (PEG) passivation layer can further suppresses random biofouling and non-specific surface adsorption on the sensing surface. Enhanced overall detection specificity can thus be achieved.

ADDITIONAL EMBODIMENTS

Embodiment 1

A device, comprising: (a) a substrate comprising a plurality of electrodes; (b) a plurality of electronic sensors integrated or assembled on said substrate and connected to said electrodes; and (c) a microfluidic component disposed on said substrate and adapted to communicate fluidically with said electronic sensors.

Embodiment 2

The device of Embodiment 1, wherein said microfluidic component comprises at least one buffer reservoir and at least one sensing arm connected to said buffer reservoir, wherein said sensing arm comprises a sample reservoir, a sample filtration module, and a sample sensing region adapted to communicate fluidically with at least one of said electronic sensors.

Embodiment 3

The device of Embodiment 2, wherein said buffer reservoir comprises at least one buffer.

Embodiment 4

The device of any of Embodiments 2 to 3, wherein said sensing arm further comprises a reference reservoir upstream of said sample sensing region, wherein optionally said reference reservoir is pre-loaded with a reference solution.

Embodiment 5

The device of any of Embodiments 2 to 4, wherein said microfluidic component further comprises at least one control arm connected to said at least one buffer reservoir, wherein said control arm comprises a control filtration module, a control sensing region adapted to communicate fluidically with at least one of said electronic sensors, and optionally a control reservoir.

Embodiment 6

The device of any of Embodiments 2 to 5, wherein said microfluidic component further comprises at least one waste reservoir connected to said sensing arm and said control arm.

Embodiment 7

The device of any of Embodiments 1 to 6, wherein said substrate comprises at least one material selected from the group consisting of a polymer and a semiconductor.

Embodiment 8

The device of any of Embodiments 1 to 7, wherein at least one of said nwFET sensors is integrated on said substrate.

Embodiment 9

The device of any of Embodiments 1 to 7, wherein at least one of said nwFET sensors is part of a chip assembled on said substrate.

Embodiment 10

The device of any of Embodiments 1 to 9, wherein at least one of said electronic sensors is a nwFET sensor that comprises a T-shaped structure comprising a latitudinal nanowire FET amplifier and a longitudinal sensing nanowire connected to said latitudinal nanowire FET amplifier.

Embodiment 11

The device of Embodiment 10, wherein said sensing nanowire, and optionally the node connecting the said sensing nanowire and nanowire FET amplifier, comprises a receptor immobilized thereon adapted to bind to a biomarker.

Embodiment 12

A device, comprising: (a) a substrate comprising a plurality of electrodes; (b) a plurality of nanowire field-effect transistor (nwFET) sensors embedded or disposed on said substrate and connected to said electrodes, wherein each of said nwFET sensors comprises a T-shaped structure comprising a latitudinal nanowire FET amplifier and a longitudinal sensing nanowire connected to said latitudinal nanowire FET amplifier, wherein said sensing nanowire, and optionally the node connecting the said sensing nanowire and nanowire FET amplifier, comprises a receptor immobilized thereon, and wherein said nanowire FET amplifier is passivated; and (c) a microfluidic component disposed on said substrate and adapted to communicate fluidically with said nwFET sensors, said microfluidic component comprising: (i) at least one buffer reservoir comprising at least one buffer; (ii) at least one sensing arm connected to said at least one buffer reservoir, said sensing arm comprising a sample reservoir, an inertial sample filtration module comprising at least one channel having a dimension larger than a cell to be filtered, and a sample sensing region adapted to communicate fluidically with at least one of said nwFET sensors; (iii)

at least one control arm connected to said at least one buffer reservoir, said control arm comprising an inertial control filtration module, a control sensing region adapted to communicate fluidically with at least one of said nwFET sensors, and optionally a control reservoir; and (iv) at least one waste reservoir connected to said sensing arm and said control arm, and wherein said microfluidic component defines a flow direction from (i) to (iv).

Embodiment 13

A method for detecting the presence of a biomarker, comprising: (A) providing a device comprising (a) a substrate comprising a plurality of electrodes, (b) a plurality of electronic sensors integrated or assembled on said substrate and connected to said electrodes, and (c) a microfluidic component disposed on said substrate and adapted to communicate fluidically with said electronic sensors; and (B) introducing a biological sample to said microfluidic component, wherein said microfluidic component directs the flow of said biological sample to contact at least one of said electronic sensors, and wherein the presence of said biomarker results in a signal change at said at least one of said electronic sensors.

Embodiment 14

The method of Embodiment 13, wherein said microfluidic component comprises at least one sensing arm connected to at least one buffer reservoir comprising at least one buffer; wherein said sensing arm comprises a sample reservoir, a sample filtration module, and a sample sensing region adapted to communicate fluidically with at least one of said electronic sensors; and wherein said biological sample is introduced into said sample reservoir to contact a stream of said buffer flowing from said buffer reservoir.

Embodiment 15

The method of Embodiment 14, further comprising releasing said buffer from said buffer reservoir before introducing said biological sample.

Embodiment 16

The method of any of Embodiments 14 to 15, wherein said sample filtration module is adapted for inertial filtration, and wherein said biological sample mixed with said buffer is filtered by said filtration module before entering said sample sensing region.

Embodiment 17

The method of any of Embodiments 14 to 16, wherein said microfluidic component further comprises at least one control arm connected to said at least one buffer reservoir; wherein said control arm comprises a control filtration module, a control sensing region adapted to communicate fluidically with at least one of said electronic sensors, and optionally a control reservoir; and wherein said biological sample is not introduced into said control reservoir.

Embodiment 18

The method of any of Embodiments 13 to 17, wherein at least one of said electronic sensors is an nwFET sensor that comprises a T-shaped structure comprising a latitudinal nanowire FET amplifier and a longitudinal sensing nanowire connected to said latitudinal nanowire FET amplifier, and wherein said sensing nanowire comprises a receptor immobilized thereon adapted to bind to said biomarker.

Embodiment 19

A method, comprising: (A) providing a device, comprising (a) a substrate comprising a plurality of electrodes; (b) a plurality of nanowire field-effect transistor (nwFET) sensors embedded or disposed on said substrate and connected to said electrodes, wherein each of said nwFET sensors comprises a T-shaped structure comprising a longitudinal sensing nanowire connected to a latitudinal nanowire FET amplifier, wherein said sensing nanowire and optionally the node connecting the said sensing nanowire and nanowire FET amplifier, comprises a receptor immobilized thereon adapted to bind to said biomarker, and wherein said nanowire FET amplifier is passivated; and (c) a microfluidic component disposed on said substrate and adapted to communicate fluidically with said nwFET sensors, said microfluidic component comprising: (i) at least one buffer reservoir comprising at least one buffer; (ii) at least one sensing arm connected to said at least one buffer reservoir, said sensing arm comprising a sample reservoir, an inertial sample filtration module comprising at least one channel having a dimension larger than a cell to be filtered, and a sample sensing region adapted to communicate fluidically with at least one of said nwFET sensors; (iii) at least one control arm connected to said at least one buffer reservoir, said control arm comprising a control reservoir, an inertial control filtration module, and a control sensing region adapted to communicate fluidically with at least one of said nwFET sensors; and (iv) one or more waste reservoirs connected to said sensing arm and said control arm, and wherein said microfluidic component defines a flow direction from (i) to (iv); (B) releasing said buffer from said buffer reservoir; and (C) introducing a biological sample to said sample reservoir to contact a stream of said buffer flowing from said buffer reservoir; wherein said biological sample mixed with said buffer is filtered by said sample filtration module before entering said sensing region; and wherein said biological sample mixed with said buffer contacts said sensing nanowire of said nwFET sensor at said sensing region, and wherein a binding between said biomarker and said receptor immobilized on said sensing nanowire results in a signal change at said at least one of said nwFET sensors.

Embodiment 20

A method for immobilizing a receptor, comprising disposing a microfluidic layer on a substrate comprising a plurality of electrodes and a plurality of nanowire field-effect transistor (nwFET) sensors connected to said electrodes, wherein said microfluidic layer comprises a plurality of channels adapted to communicate fluidically with said nwFET sensors; and adding a solution of said receptor into at least one of said channels, wherein said receptor contacts and binds to at least one of said nwFET sensors.

Embodiment 21

The device of any of Embodiments 1 to 12, further comprising an interface for connecting to an electronic device, such as a laptop or a smart phone.

Embodiment 22

The method of any of Embodiments 13 to 19, further comprising connecting the test device with an electronic device, such as a laptop or a smart phone, via an interface to access test results.

WORKING EXAMPLES

Example 1

A T-nwFET sensor as shown in FIG. 3 was fabricated on silicon-on-insulator (SOI) wafer substrates using standard integrated circuit fabrication processes. First, the SOI layer was thinned to 50 nm and patterned into T-shape nanowire structures with width ranging from 50 nm to 3 µm using electron beam lithography. Next, the source, drain, and base metal electrodes were formed by photoresist lift-off of a sputtered platinum-on-titanium dual layer. Finally, all the fabricated sensors were covered with a layer of silicon nitride, except above the sensing nanowire surface, to passivate them from any interaction with the analyte solution during the detection measurements. Generic FET sensors with just an I-shape sensing nanowire channel (denoted as I-nwFET) of the same width and length were co-fabricated for control purposes.

First validated were the acceptable baseline electrical characteristics of the fabricated T-nwFET sensors. After immobilization of respective specific monoclonal antibody receptors on the sensing nanowire surface, preliminary label-free and real-time immunodetection of prostate-specific antigens (PSA) and cardiac troponin I (cTnI) were performed in low-salt buffer.

Figure 5:
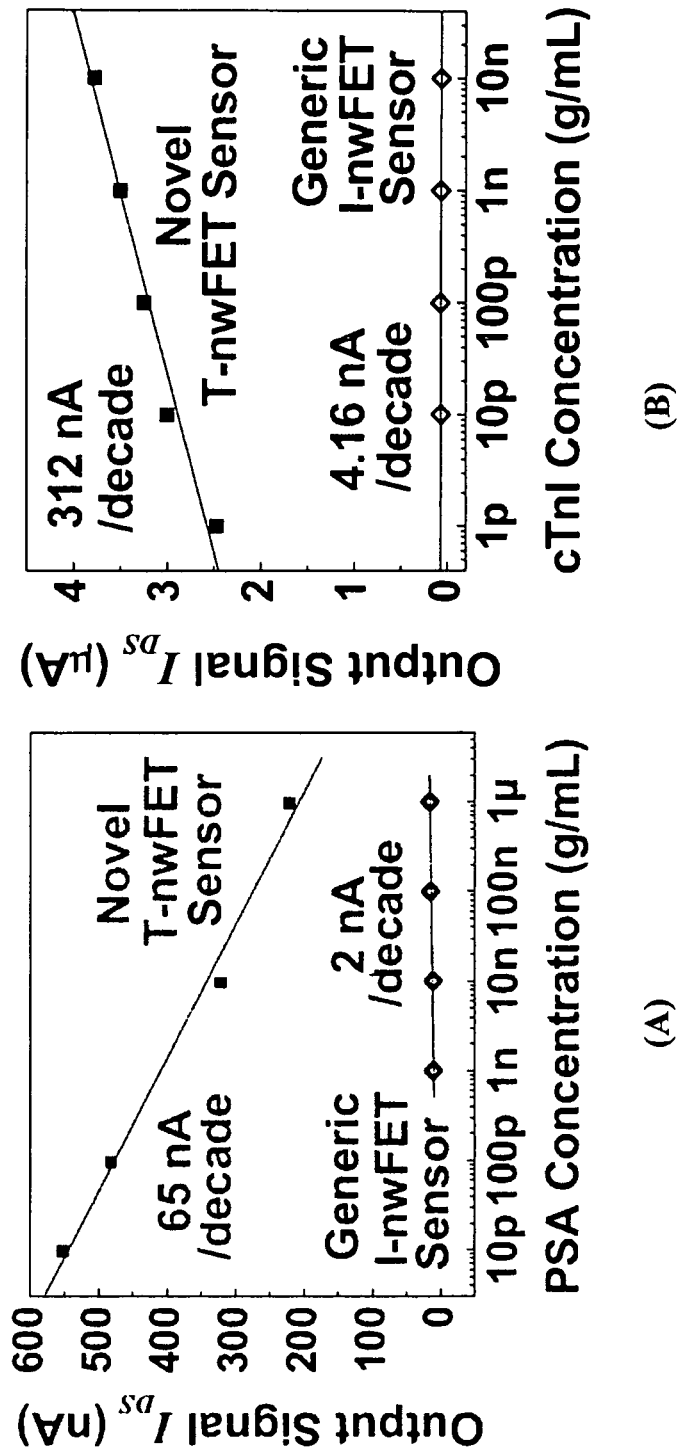
FIG. 5 shows high sensitivity detection of PSA (A) and cTnI (B) using an example of T-nwFET sensors.

The pre-optimized T-nwFET LOC sensors exhibited a lower LOD of few pM (with practically high current levels) and ~32-75× sensitivity boost over the generic I-nwFET sensor, as shown in FIGS. 5A and 5B. The sensitivity and DR of the T-nwFET sensor can be adjusted via structural design and/or voltage biasing at runtime if needed for tailored multiplexing applications.

Figure 6:
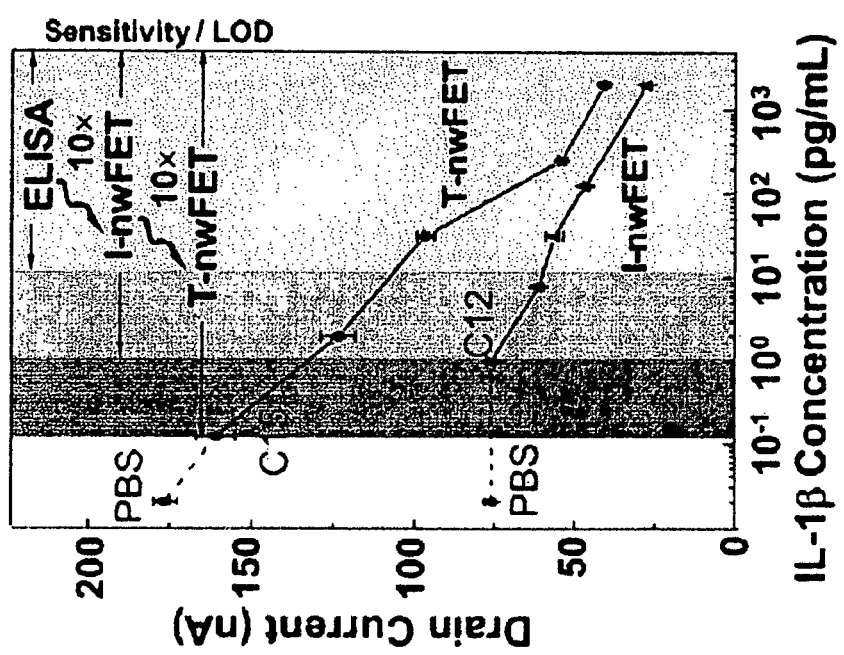
FIG. 6 shows a side-by-side comparison in cytokine (IL-1β) detection using commercial ELISA kit and an example of a T-nwFET LOC sensor. The T-nwFET sensor exhibits roughly 2 orders of magnitude lower limit of detection (LOD) over ELISA (and about 10× lower LOD over the I-nwFET sensor control).

In addition, a side-by-side comparison between the novel T-nwFET LOC sensor and commercial ELISA kit was conducted for cytokine detection. For specific detection of interleukin-1 beta (IL-1β), human anti-IL-β monoclonal antibody was immobilized onto the sensing nanowire followed by the introduction of analyte with increasing concentrations. As shown in FIG. 6, the commercial ELISA kit demonstrated an LOD of around 0.9 pM extracted via optical density. On the contrary, the T-nwFET sensor delivered an LOD of around 7 fM (denoted as C15) which is roughly 2 orders of magnitude better than ELISA. It is also noted the T-nwFET sensor's LOD is about 10× lower than the I-nwFET control, as shown in FIG. 6.

Example 2

Besides the sensitive and robust sensing platform hardware, a runtime calibration scheme was developed for reliable assay operation in the presence of intrinsic device variability. The scheme used is a curve-fitting based approach that involves multiple input reference solutions with known concentration together with the blind sample—the reference solutions and the sample were sequentially introduced, in an ascending concentration order, to the same biosensor for interpolating the blind sample's true concentration.

The concentrations of reference solutions were somewhat below (and above) the expected concentration of the sample; these solutions were introduced to the same biosensor in an ascending concentration order and before (and after) the sample introduction given the much stronger equilibrium binding than dissociation in such highly specific antigen-antibody immunoreactions. In this regard, the 100× lower detection limit of the T-nwFET biosensors uniquely permits detection of the lower references. Also, such multiple solution introductions and bindings onto the same sensing surface are likely impractical in most labeling-based assays.

Figure 11:
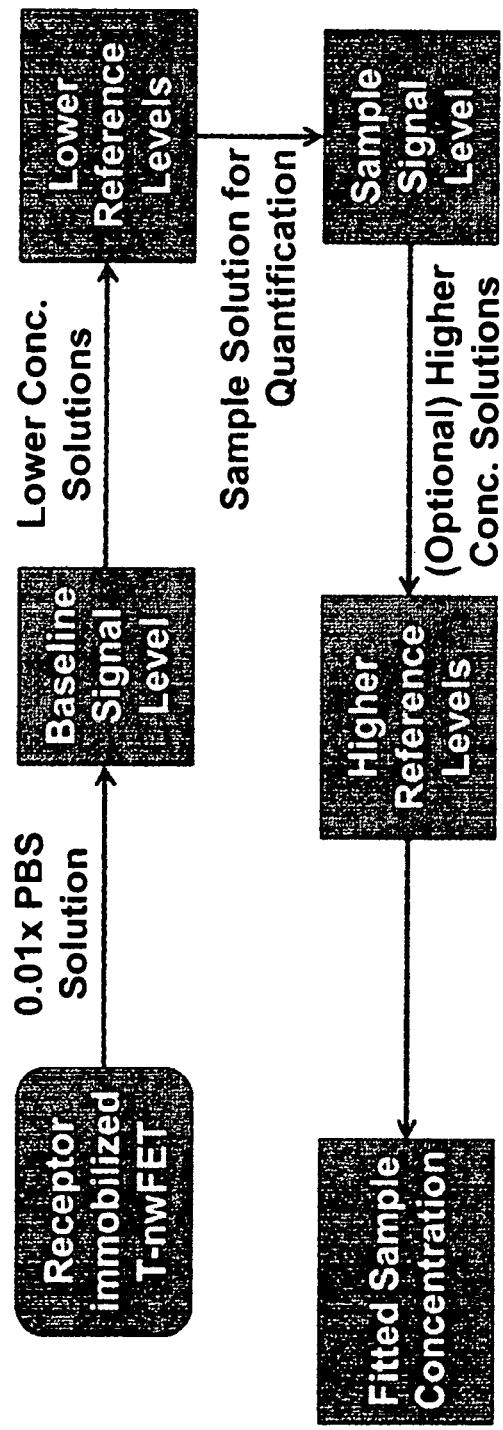
FIG. 11 shows example procedures to implement a runtime self-calibration scheme using reference solutions with known concentrations.
Figure 12:
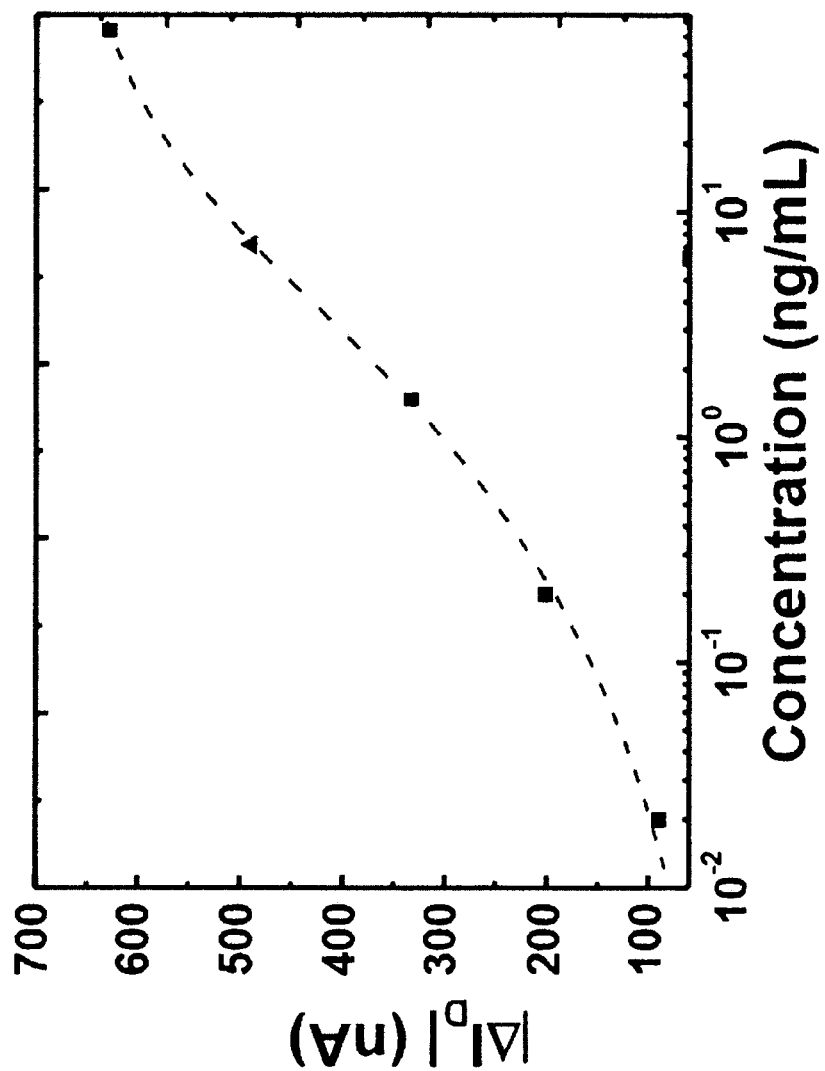
FIG. 12 shows example self-calibration results. The black squares are from known concentration target analyte reference solutions. The red triangle is from a blind analyte sample.

The procedure for implementing the proposed runtime self-calibration scheme is shown in FIG. 11. On each receptor pre-immobilized T-nwFET biosensor, a PBS buffer solution was first introduced to establish the baseline output signal level. Then the lower known concentration target analyte reference solutions were sequentially introduced, followed by the actual sample introduction. Since these reference concentrations are somewhat lower than the expected sample concentration, there should not be any binding competition to interfere with the quantitation process. As an option, additional reference solutions with higher known target analyte concentration than the expected sample concentration were introduced to establish the upper references. The true sample concentration was quantified via interpolation based on the reversible binding reaction models at equilibrium state. The fitting parameters are there to handle all practical variations mentioned above, which values were deduced from the lower and higher known concentration references. An exemplary fitting result validating the original runtime self-calibration scheme on the label-free optics-free T-nwFET biosensors is shown in FIG. 12.

What is claimed is:
1. A method for detecting an analyte, comprising:
   providing a device comprising: (a) a substrate comprising a plurality of electrodes; (b) a plurality of electronic sensors integrated or assembled on said substrate and connected to said electrodes; and (c) a microfluidic component disposed on said substrate and adapted to communicate fluidically with said electronic sensors;
   providing a first reference point for said device, providing said first reference point comprising obtaining a first signal change in said device by contacting said device with a first reference solution comprising a first predetermined reference concentration of said analyte;
   providing a second reference point for said device, providing said second reference point comprising obtaining a second signal change in said device by contacting said device with a second reference solution comprising a second predetermined reference concentration of said analyte, said first predetermined reference concentration being different from said second predetermined reference concentration;
   contacting said device with a biological sample comprising said analyte having an expected concentration range in said biological sample, wherein the presence of said analyte in said biological sample results in a third signal change in said device;
   providing a third reference point for said device, providing said third reference point comprising obtaining a fourth signal change in said device by contacting said device with a third reference solution comprising a third predetermined reference concentration of said analyte; and quantifying a concentration of said analyte in said biological sample based on said third signal change, said first reference point, said second reference point, and said third reference point, wherein each of said first predetermined reference concentration and said second predetermined reference concentration is lower than said expected concentration range of said analyte in said biological sample, said third predetermined reference concentration is higher than said expected concentration range of said analyte in said biological sample, and said first reference solution, said second reference solution, said biological sample, and said third reference solution are contacted with said device in an ascending concentration order of said analyte.

2. The method of claim 1, wherein quantifying said concentration of said analyte in said biological sample comprises interpolating said concentration from a fitted curve based on said first reference point said second reference point, and said third reference point.

3. The method of claim 1, wherein at least one of said electronic sensors is a nanowire field-effect transistor sensor comprising a T-shaped structure comprising a latitudinal nanowire FET amplifier and a longitudinal sensing nanowire connected to said latitudinal nanowire FET amplifier.

* * * * *